United States Patent [19]

Andersson et al.

[11] Patent Number: 5,752,828
[45] Date of Patent: May 19, 1998

[54] ARRANGEMENT FOR PROSTHETIC CONSTRUCTION UNIT AND IMPLANT

[75] Inventors: Matts Andersson, Lerum; Ulf Johansson, Onsala, both of Sweden

[73] Assignee: Nobel Biocare AB, Gothenburg, Sweden

[21] Appl. No.: 537,758

[22] PCT Filed: Feb. 14, 1995

[86] PCT No.: PCT/SE95/00148

§ 371 Date: Dec. 5, 1995

§ 102(e) Date: Dec. 5, 1995

[87] PCT Pub. No.: WO95/22939

PCT Pub. Date: Aug. 31, 1995

[30] Foreign Application Priority Data

Feb. 24, 1994 [SE] Sweden .................. 9400631

[51] Int. Cl.$^6$ .................................................. A61C 8/00
[52] U.S. Cl. .................................... 433/172; 433/173
[58] Field of Search ................................ 433/173, 174, 433/175, 176, 193, 172

[56] References Cited

U.S. PATENT DOCUMENTS

| | | | |
|---|---|---|---|
| 4,713,003 | 12/1987 | Symington et al. | 433/173 |
| 4,850,869 | 7/1989 | Steinfort et al. | 433/193 |
| 4,872,840 | 10/1989 | Bori | 433/173 |
| 4,988,292 | 1/1991 | Rosen | 433/173 |
| 5,049,073 | 9/1991 | Lauks | 433/173 |
| 5,145,372 | 9/1992 | Daftary et al. | 433/173 |
| 5,199,873 | 4/1993 | Schulte et al. | 433/174 |
| 5,242,303 | 9/1993 | De Buck | 433/173 |

Primary Examiner—Cary E. O'Connor
Attorney, Agent, or Firm—Pollock, Vande Sande & Priddy

[57] ABSTRACT

An apparatus for fixing a prosthetic construction unit to an implant comprises one or more implant control parts; one or more construction unit control parts cooperating with the one or more implant control parts to impart to the unit a distinct position on the implant; recesses in the one or more implant and construction unit control parts; and a securing element, for installing in the recesses of the one or more implant and construction unit control parts to extend in an essentially transverse direction to the implant. The securing element, when in the installed position, creates a pressing force against the one or more construction unit control parts opposite a pressing force created against the one or more implant control parts in an axial direction of the unit and the implant for pressing the unit against the implant.

21 Claims, 4 Drawing Sheets

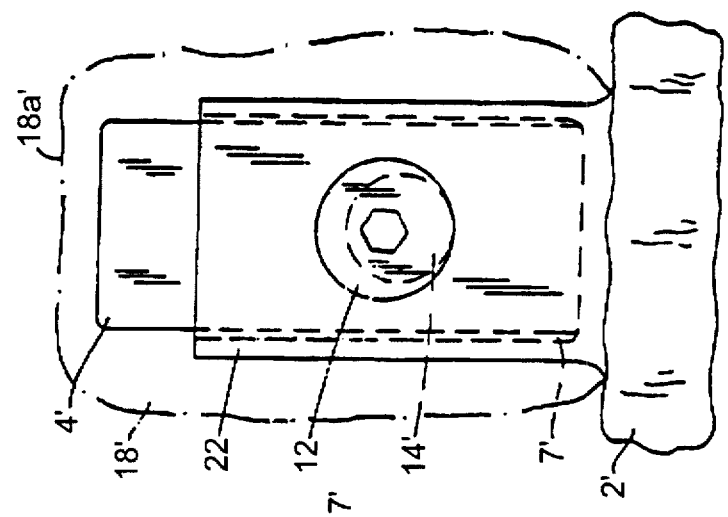
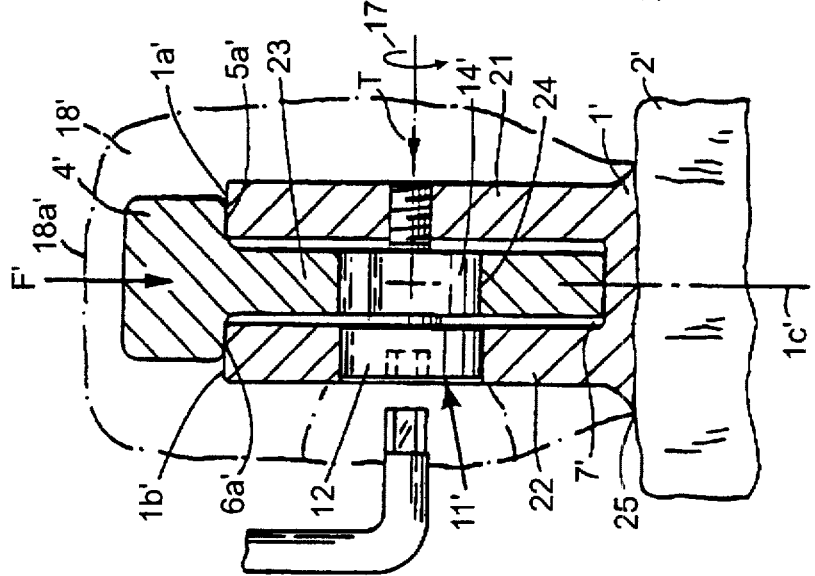
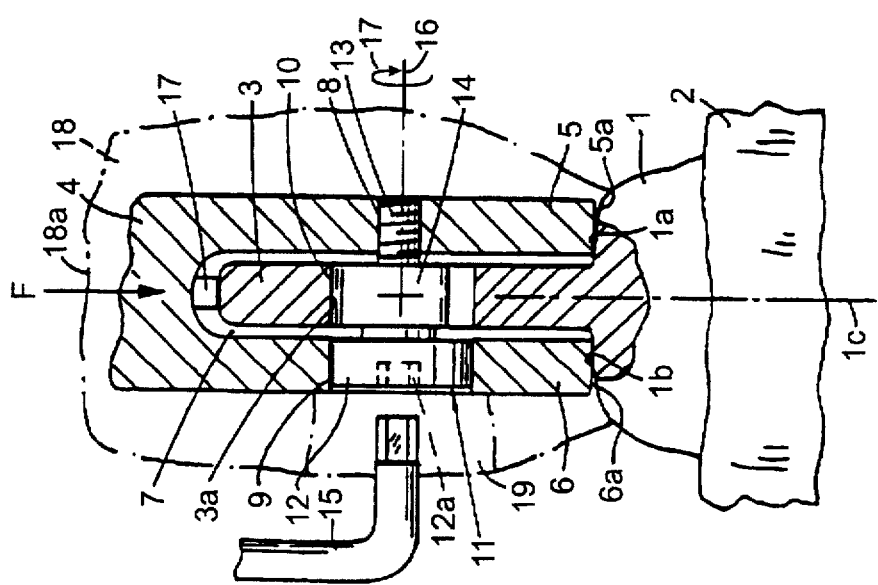

5,752,828

ARRANGEMENT FOR PROSTHETIC CONSTRUCTION UNIT AND IMPLANT

TECHNICAL FIELD

The present invention relates to an arrangement for fixing a prosthetic construction unit to an implant. Examples of implants which may be mentioned are those formed in the dentine.

BACKGROUND OF THE INVENTION

It is already known to anchor prosthetic constructions, such as dental caps, dental bridges, dental bridge parts, etc., to one or more implants. The actual anchoring is effected by screws which are screwed essentially in the axial direction of the implant.

In the proposed application screws, often emerge in parts of the construction which are exposed, for example chewing surfaces which are exposed to considerable forces (chewing forces). Even if the respective screw head is covered over with material, there may be problems in obtaining optimal strength in the constructions, and there may be difficulties, from the technical point of view, in achieving an optimal external shape, satisfactory appearance, etc. The invention solves this problem, among others.

There is also a requirement to use anchoring elements of types other than screws, which in some cases can be of critical importance for establishing a reliable anchoring force, and the material of which screws should last for the long period of use of the prosthesis in question. Thus, for example, the limits of elasticity of the screws may be exceeded, which leads to a deterioration in the quality of the anchoring function, and has a weakening effect difficult to detect. The present invention solves this problem too.

Furthermore, there is a need to establish a simplified technique for anchoring prosthetic constructions to implants. The present invention solves this problem too.

The characterizing feature of the present invention is that the unit and the implants comprise control parts which can cooperate with each other and which are intended, when they are brought together, to impart to the unit a distinct position on the implant. Further characteristics are that the said control parts on the unit and the implant are designed with recesses arranged to receive an element which extends essentially in the transverse directions of the implant and of the unit and which, in the applied position, bears in the one control part of the said control parts and acts on the other control part such that a pressing force, acting in the axial directions of the unit and of the implant, is obtained for pressing the unit against the implant.

In further developments of the inventive concept, the element is designed with an eccentric part which, in a first position of rotation of the element, allows the element to be applied in the recesses of the control parts, and, in one or more other positions of rotation, presses against a cooperating surface on either of the control parts. The element can in this case preferably have a dual bearing in the first control part. Thus, in its dual-bearing suspension, the element cooperates with the other control part via the eccentric part. The control part secured to the implant can preferably have one or more spaces or compartments which extend in the at least essentially longitudinal extent of the implant and in which the control part(s) of the construction unit can be applied. In a corresponding manner, the control part of the construction unit can instead comprise one or more compartments in which the control part(s) of the implant bear(s).

In one embodiment, the element can comprise a head-shaped part which can be mounted in a recess in a first portion of the one or the first control parts. The element can also comprise a pin-shaped part which can be mounted in a second portion of the said first control part or control parts. The said eccentric portion is arranged between the said head-shaped and pin-shaped parts. The head-shaped portion preferably has a central recess, of square or hexagonal shape, via or with which the element can be rotated about its longitudinal axis using a tool of a type which is known per se.

The implant or the unit can comprise two parts or plates which are arranged in parallel and which can be pushed over a corresponding part or plate in the implant or the unit, respectively. in one embodiment, the recess in which the said pin-shaped part bears can be provided with an internal thread which preferably has only a small number of turns. At its free end, the pin-shaped element is provided with an external thread which cooperates with the said internal thread. In this case, the thread function will be activated in conjunction with simultaneous activation of the eccentric part of the element against the relevant cooperating surface on either of the control parts. The eccentric part can be designed with ridges of different radii in relation to the axis of rotation of the element in order to establish, in each case of use, an optimal pressing force for pressing the unit against the implant.

The element can also be designed without an eccentric part, i.e. as a straight, pin-shaped part. The control parts are in this case arranged with a first assembly position in which the recesses in the respective control part are located slightly eccentrically in relation to each other. By means of the pressing-in of the pin-shaped element in the transverse direction, the eccentricity is nullified, and at the same time the fastening force is established. The eccentricity is in this case set in relation to the desired pressing force. In one and the same case of use, different pin-shaped elements with slightly different diameters can be used, a first pin-shaped element giving a first pressing force, a second pin-shaped element giving a second pressing force, and so on. Elastic members, glue, etc. can be used in connection with the above.

By means of what is proposed above, a good function for the clamping force can be guaranteed, and clamping forces of the order of magnitude of 100–200N can be established. The connection surface between the construction unit and the implant can be located at a higher level than before. The transverse positioning of the element can be established so that the head-shaped part emerges at a less sensitive or critical surface, where, for example, the covering material is not exposed in the same way as before. Fastening elements other than screws can be used in this context, for less critical fastening methods where the tightening or clamping force can be determined with great accuracy.

BRIEF DESCRIPTION OF THE DRAWINGS

A presently proposed embodiment of an arrangement having the features characteristic of the invention will be described below, with reference to the attached drawings, in which:

FIG. 1 shows, in vertical section and from the side, the clamping of a construction unit in an implant, FIG. 2 shows, in a vertical view and from the side, another embodiment of the clamping principle in relation to that in FIG. 1, FIG. 3 shows, in a vertical view and from the rear, the clamping principle according to FIG. 2.

DETAILED DESCRIPTION OF THE PREFERRED EMBODIMENTS

Figure 4:
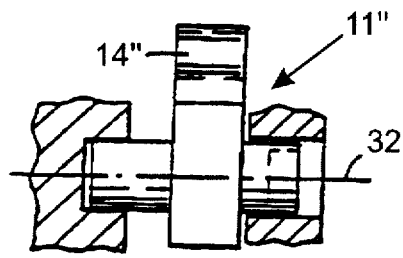
FIG. 4 shows, in longitudinal section, the construction of a tightening element.

In FIG. 1, the upper part of an implant is shown by 1. The implant is designed in a known manner and can comprise a spacing member, for example at the upper parts. In this case, the anchoring is effected in the dentine 2. A first control part 3 is fastened to the implant. The fastening can be effected in a known manner, and the implant can, for example, form part of a spacing member belonging to the implant 1. A construction unit is represented by 4 in FIG. 1. The construction unit is provided with a second control part which includes a first part 5 and a second part 6. In this embodiment parts 3, 5 and 6 include plate-shaped parts which protrude into or over each other. The parts 5 and 6 have bottom surfaces 5a and 6a, respectively, which are arranged to bear against corresponding top surfaces 1a and 1b, respectively, on the implant or its spacing member, etc. The parts 5 and 6 can form a compartment or a recess 7 in which the part 3 extends. The compartment 7 surrounds the part 3 from all sides. The parts 5 and 6 include recesses 8 and 9, and the part 3 includes a recess 10. Arranged in the recesses is an element 11 which has a head 12, mounted in the recess 9, a pin-shaped part 13 mounted in the recess 8, and an eccentric part 14 mounted in the recess 10. The head is provided with a central, outwardly opening recess 12a via which a key 15 can cooperate for turning the element about its longitudinal axis 16 in the direction of the arrow 17. The recess 8 and the pin-shaped part are provided with mutually cooperating threads in accordance with what is described below. In one embodiment, the threads can be omitted.

The recesses 8, 9 and 10 and the element are arranged such that the element can be applied in its position in the recesses and turned using the tool 15. Upon turning, the eccentric part 14 comes into cooperation with a bottom surface 3a on the part 3. A pressing force F arises and presses the construction part against the implant via the surfaces 5a, 6a and 1a, 1b, respectively. The eccentric part 14 is designed in this case such that distinct positions of rotation can be obtained for the element 11, providing for a distinct fastening of the construction unit 4 in the implant 1. The pressing force is directed in the axial direction 1c of the implant. In one embodiment, the pressing force can be applied counter to the action of an elastic element 17. Glue or another fastening means can also be applied in the recess 7 to ensure that the construction unit is positively anchored to the implant 1. Any release of the construction unit can subsequently take place via or by means of the spacing member in the implant 1. In the figure, the material added to the tooth, or the outer material which is applied on the construction unit 4, is indicated by 18. The head of the fastening element can be covered with material 19. In FIG. 1, the recess 8 has been shown as continuous through the part 5. In one embodiment, the recess need not be continuous.

In the embodiment according to FIG. 2, the implant 1' has instead been provided with two parts 21, 22 in its control element, and the construction unit 4' has has been provided with a part 23. Parts 21, 22 and 23 cooperate in a manner which corresponds to the parts 3, 5, 6 in the embodiment according to FIG. 1. The fastening element 11' in this case cooperates, via its eccentric part 14', with a bottom surface 24 so that, the force F' arises in the axial direction 1c' in a manner corresponding to the case according to FIG. 1. The direction of rotation 17' is optional, as in FIG. 1. In FIG. 2, the connection surfaces 1a', 1b' and 5a', 6a', respectively, have been shifted upwardly towards the free end 18a' of the tooth. An area 25 at the point where the implant merges with the dentine is thus without any intermediate gap between the construction unit and the implant. In this case too, the recess 7' surrounds the part 23 on all sides.

FIG. 3 shows the aforementioned surrounding and design of the actual parts which are evident in FIG. 2.

Figure 5:
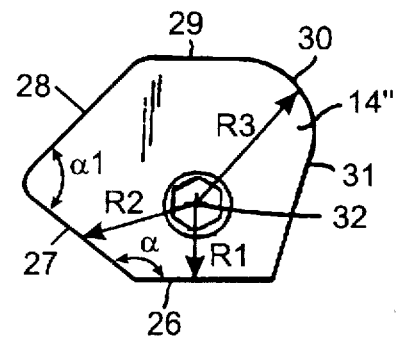
FIG. 5 shows, in an end view, the element according to FIG. 4.
Figure 6:
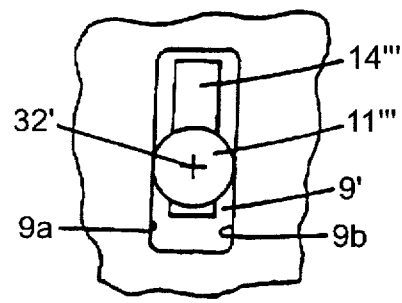
FIG. 6 shows, in a side view, the design of a recess in a control element according to FIGS. 1 or 2.

FIGS. 4, 5 and 6 show examples of designs of the fastening element 11". The design of the eccentric part 14" this embodiment is evident from FIG. 5. The eccentric part has a number of sides and bends 26, 27, 28, 29, 30 and 31. The axis of rotation of the fastening element is indicated by 32, and it is evident from FIG. 5 that the surfaces and bends are at different distances R1, R2, R3 from the axis. The side surfaces can have different angles α, α1, etc. The curved shape of the bend 30 can also vary at different positions. It will be seen that by selecting the distances of the surfaces from the center, their different inclinations, the bends, etc., it is possible to obtain a clamping force for the units according to FIGS. 1 to 3 as a function of the rotational position of the fastening element about the axis of rotation 32. It will also be seen that distinct positions can be obtained for the clamping forces. Manufacturing irregularities in the control parts can be compensated by different degrees of rotation of the element, and so on. In FIGS. 1 to 5, surfaces, gaps, angles, etc., have been shown exaggerated in size in order to ensure that the presentation of their function is clear. It is obvious that, for example, the play between the control parts must be adapted to the accuracy which is required in the case in question.

FIG. 6 shows a further embodiment of the element 11'''. It also shows the shape of a recess 9', via which the element is introduced. In order to allow the eccentric part 14''' to take up a first rotational position for the element about the axis of rotation 32', the recess 9'is of rectangular design. The element can be turned from the position shown in FIG. 6 to one or more other rotational positions in which there is cooperation with the control part or control parts in question. The head-shaped part on the fastening element is guided against inner surfaces 9a, 9b (long sides of the rectangle).

Figure 7:
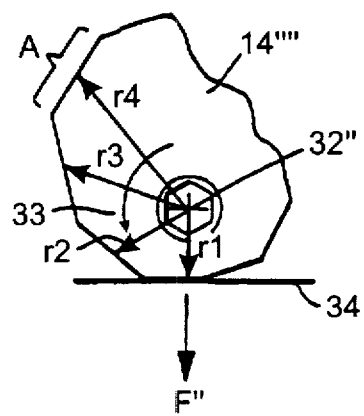
FIG. 7 shows, in an end view, the construction of an eccentric part of a tightening element.

FIG. 7 shows another embodiment of the eccentric part 14''''. A rotational movement 33 about the axis 32'' leads to an increased pressing force F'' as a function of the rotation about the axis 32''. The distances or the radii r1, r2, r3 and r4 increase in steps, and a certain length A of the peripheral straight surfaces (ridges) ensures a distinct bearing against the relevant surface 34 of the control part in question.

Figure 8:
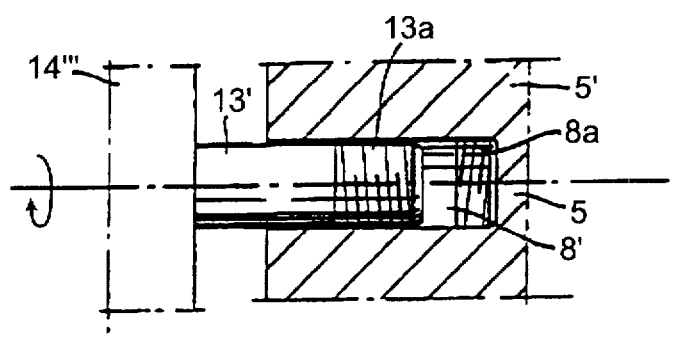
FIG. 8 shows, in longitudinal section, parts of a tightening element, and the construction of a control part in which the tightening element can be fastened.

FIG. 8 shows can the pin-shaped part 13' can provided with an external thread 13a at its free end. This external thread can cooperate with an internal thread 8a on, for example, the part 5'. In this case, the recess 8' is not continuous, but instead has a cover part. A characteristic feature of the thread arrangement is that the internal thread includes only a small number, a pair of turns, with which the element cooperates in the final stage of its application.

Figure 9:
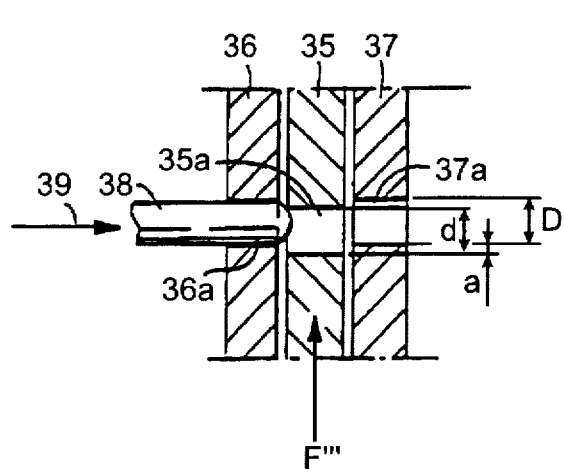
FIG. 9 shows, in a vertical section, another fastening principle in relation to FIGS. 1 to 8.
Figure 10:
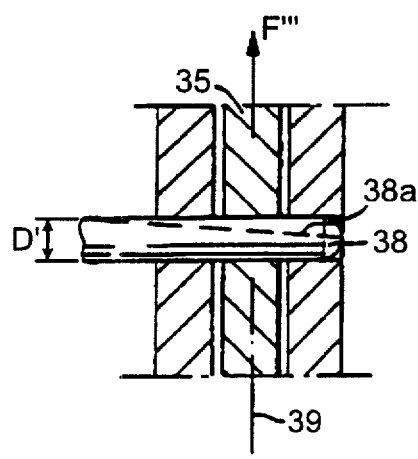
FIG. 10 shows, in a vertical section, a second stage of the fastening principle according to FIG. 9, and FIGS. 11–11c show, in vertical sections and views, a further constructional embodiment, with associated parts.

FIGS. 9 and 10 show another fastening principle. The control parts include, in conformity with what is described above, the parts 35 and 36, 37, respectively. The recesses or the holes 35a and 36a, 37a, respectively, are in this case arranged eccentrically in relation to each other in a first application position, that is, in the position according to FIG. 9, between the parts 35 and 36, 37, respectively. The diameters d and D, respectively, of the recesses are of substantially the same size. In the first position, the recesses are arranged slightly eccentrically in relation to each other, which eccentricity has been indicated in FIG. 9 by the distance a. In this case, use is made of a pin-shaped part 38 which can be inserted into the recesses 36a, 35a and 37a in the direction of the arrow 39.

FIG. 10 shows complete insertion into the recesses, and it can also be seen that the eccentricity has been reduced or eliminated, and at the same time a pressing force F''' has been obtained, for example in the part 35, in a direction 39 which coincides with the axial direction in accordance with the above. A relative movement between the parts 35 and 36, 37 thus occurs upon insertion of the element 38 into the recesses. The magnitude of the movement and of the clamping force F''' are determined by the eccentricity and the diameter D' of the pin-shaped element. Different clamping forces F''' can be obtained by using different pin-shaped elements 38 with different diameters D', and so on. In this case, the element 38 need not be designed as a cylindrical pin, but instead can have different shapes, for example a wedge shape, which is shown, in FIG. 10, by the broken line 38a, and so on. The above can be used in combination with snap arrangements, material deformations in the element and/or the control parts, all for the purpose of defining a longitudinal displacement position for the element in the recesses. When the element has a wedge shape, the surfaces cooperating with the element can be inclined to an extent corresponding to the angle of the wedge, and so on. In this case there can be, with an essentially transverse direction T, an angle deviation of, for example, ±10° in relation to the line perpendicular to the axial direction. Likewise, the element can be angled slightly in relation to the front-to-back direction of the respective tooth/tooth replacement, with a corresponding value.

Figure 11:
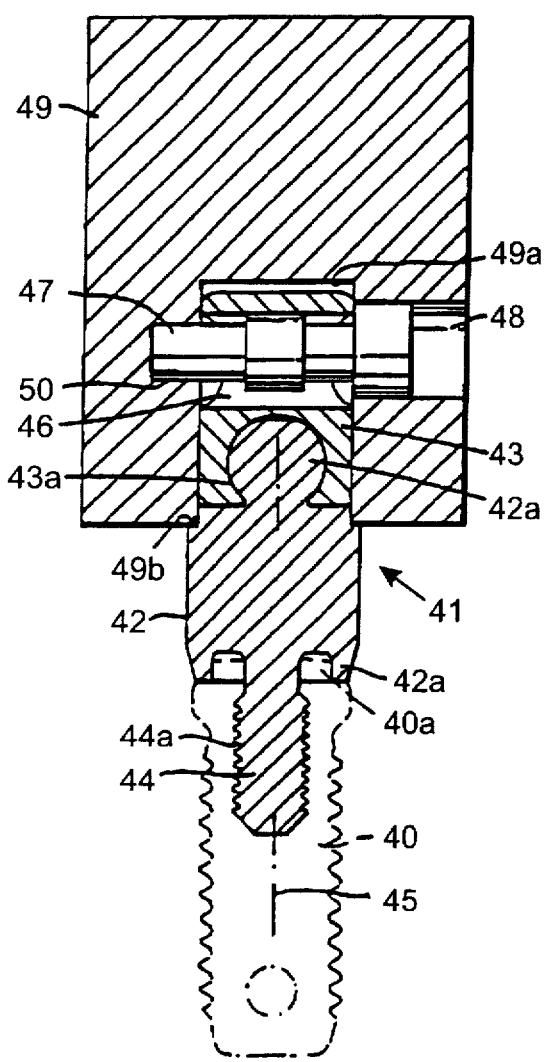
Figure 11C:
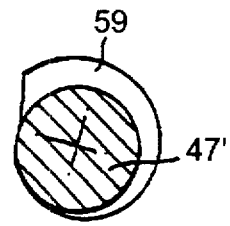
Figure 11A:
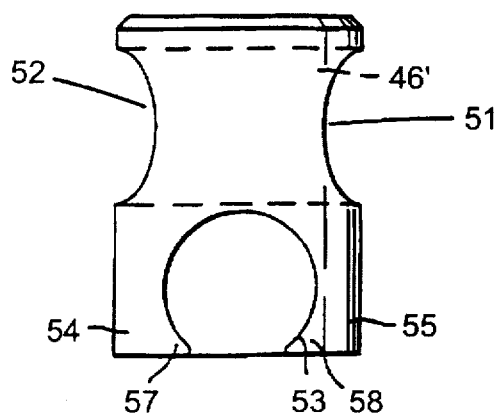
Figure 11B:
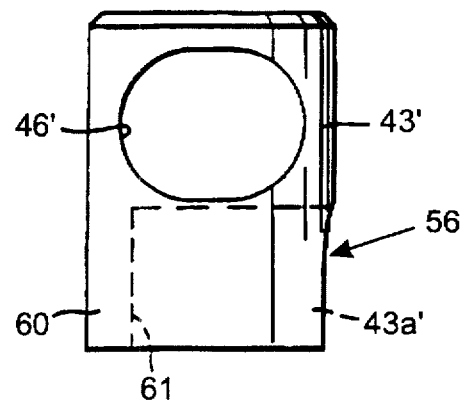

A synonym for each control part mentioned above is bypass part. In FIG. 11, the implant is shown by 40, and the control part or bypass part belonging to the implant is shown by 41. The part 41 consists in this case of two mutually lockable parts 42 and 43. The part 42 is secured in the implant 40 by a part 44 which can consist of a screw-shaped part having a thread 44a, which cooperates with a corresponding thread in the implant. The part 42 has a preferably spherical portion 42a. The part 43 includes a recess 43a which corresponds to the spherical portion and via which the part 43 can be fitted on the spherical portion.

The parts 42 and 43 can thus assume different positions of rotation about their longitudinal axes 45 before they are locked to each other. The part 43 has the transverse recess for the transverse element 47 which is passed via the transverse recess 48 in the construction unit 49. Thus, the part 43 can be adapted in terms of its angle position (about the longitudinal axis 45) to the recess 48 and the recess 50 in the construction unit 49 independently of the angle of rotation of the implant and the part 42, before the parts are locked to each other. In this way, the positions of the recesses 48, 50 on the tooth/tooth replacement can be given a desired direction, and thus, for example, the mouth 48 can be directed towards the inside of the respective tooth.

In order to facilitate entry of the element 47 into the recesses 46, 48 and 50, the recess 46' in the part 43' is widened (oval) in the transverse direction for obtaining a guide-in function for the element 47, such that the part 43' can turn upon insertion of the element, before the parts are locked to each other. Both the mouths 51 and 52 of the recess 46' have these oval, widened shapes. The recess 43a' is open at the bottom and engages with an inner surface part 53 about the ball or the spherical portion 42a. The part 43' thus has two downwardly projecting legs 54, 55 which present the inner surface part 53. The recess 43a' exhibits a mouth 56 which extends sidewards and via which the part 43' can be fitted over the portion 42a. The legs 54 and 55 are thus each provided with a widened part 57 and 58, respectively. The element 47 has an eccentric part 59 of the "Archimedes type". In order to ensure that the legs 54, 55 will not be spaced apart during connection and lose their grip on the spherical portion or the ball, they are held together at one end of the recess 43a' by a gable portion 60 which has an inner wall 61 of the recess 43a'.

The application of the construction unit proceeds as follows. The part 42 is secured in (screwed into) the implant 40. The part 42 has a downwardly projecting edge 42a which closes tightly against the top surface of the implant. The implant can be provided with a central guide part 40a. The part 43 is then fitted on the part 42 via the portion 42a and the recess 43a, 43a'. The construction unit is then fitted over the part 43 via its recess 49a. The application of the parts to each other is in this case carried out such that the mouth 48 is given the correct direction in the oral cavity/on the tooth or the tooth replacement, and such that the recesses 46, 48 and 50 are placed in an essentially straight line in relation to each other. The element 47 is then introduced into the recesses via the recess 48 with the cam 59 in a first angle of rotation, in which there is no cooperation with the inner wall of the recess 46. The construction unit has inner guide edges 49b which come into cooperation with corresponding guide surfaces on the part 42. The part 43 is matched in shape to the recess 49a and, as a result of this, is guided in terms of its angle of rotation in relation to the unit 49. The construction unit 49 and the implant 45 are adapted to each other, in terms of angle of rotation about the longitudinal axes 45, by means of the adjustment of the angle of rotation about the axes 45 between the parts 42 and 43.

The element 47, 47' is then turned through an angle so that the cam 59 cooperates with the inner wall of the recess 46. A final adjustment is thus made between the unit 49 and the parts 42 and 43. The securing between the unit 49, the parts 42, 43 and the implant is determined by the torsional force on the element 47 (see above).

The invention is not limited to the embodiment shown above by way of example, but can instead be modified within the scope of the attached patent claims and the inventive concept.

We claim:

1. An apparatus for fixing a prosthetic construction unit to an implant said apparatus comprising
   at least one implant control part;
   at least one prosthetic construction unit control part cooperating with said at least one implant control part to impart to the prosthetic unit a distinct position on the implant;

at least one recess in each of said implant and construction unit control parts; and a securing element for installing in said recesses of said implant and construction unit control parts to extend in an essentially transverse direction to the implant;

wherein said securing element, when in the installed position, creates a pressing force against said construction unit control parts opposite a pressing force created by the securing element against said at least one implant control part in an axial direction of the unit and the implant, for pressing the construction unit against the implant; and wherein said securing element comprises a dual bearing in said at least one of said implant and unit control part and can cooperate, in its dual bearing suspension, with the other one of said implant and prosthetic construction unit control part via an eccentric part.

2. An apparatus according to claim 1 wherein said securing element comprises said eccentric part which, in a first rotational position permits installation of the securing element in said recesses of said implant and construction unit control parts, and in at least one other rotational position, presses against cooperating surfaces of said implant and construction unit control parts.

3. An apparatus according to claim 2 wherein said securing element further comprises:

a head-shaped part at one end of said securing element, and a pin-shaped part at a second end of said securing element, and said eccentric part is arranged between said head-shaped and pin-shaped parts.

4. An apparatus according to claim 3, wherein said head-shaped part comprises a central recess for rotating said securing element about its longitudinal axis from said first rotational position of said eccentric part to said second rotational position.

5. An apparatus according to claim 3 wherein the securing element is provided at its second end with an external thread which, when mounted in said control unit or implant control part, cooperates with an internal thread in the recess of said implant or construction unit control part.

6. An apparatus according to claim 2 wherein the eccentric part comprises multiple surfaces of differing radii defined from the axis of rotation of the securing element and wherein a surface having a greater radius of a preceding surface on the eccentric part increases the pressing force on the control units as the securing element is rotated from a surface of lesser radius.

7. An apparatus according to claim 1 wherein each of said implant control parts has at least one space or compartment which extend in the at least essentially longitudinal direction of the implant and in which said at least one construction unit control part is applied.

8. An apparatus according to claim 1 wherein said implant control part has two portions which are arranged in parallel and which can be pushed over said construction unit control part.

9. An apparatus according to claim 1 wherein either said implant control part or said construction unit control part includes two portions arranged in parallel, and wherein, when the unit is fixed to the implant, the two portions of said implant control part or said construction unit are displaced parallel to and over cooperating portions of said implant control part or said construction unit control part.

10. An apparatus according to claim 1 wherein said implant and construction unit control parts further comprise:

a first assembly position prior to installation of the securing element in which said recesses are slightly eccentric in relation to each other, and a second assembly position after installation of the securing element, in which said recesses are, by means of alignment by the securing element, essentially concentric in relation to each other.

11. An apparatus according to claim 1 further comprising at least one elastic element between the construction unit and implant control part, said at least one elastic element creating forces counter to said pressing forces.

12. An apparatus according to claim 1 further comprising adhesive means located between the construction unit and implant control parts for assisting the securing element in anchoring said control parts relative to each other.

13. An apparatus according to claim 1 wherein said securing element is installed in said implant control parts at any angle of rotation of said implant control parts about their longitudinal axis.

14. An apparatus according to claim 1 wherein an implant control part comprises first and second locking portions, said locking portions being coupled to each other.

15. An apparatus according to claim 1 wherein an implant control part comprises:

a first locking portion having a spherical portion and a second locking portion having a corresponding spherical recess for coupling said portions together at an angle of rotation about a longitudinal axis of the first and second portions, said second locking portion having a recess which extends in an essentially transverse direction from said implant control part, said recess forming a recess for installing said securing element.

16. An apparatus according to claim 15 wherein said second locking portion recess comprises:

oval mouths for assisting in rendering said second locking portion independent of said mutual angle of rotation upon entry of the securing element into the recesses.

17. An apparatus according to claim 1 wherein said securing element has a continuously rising Archimedes type curved shape.

18. An apparatus for fixing a prosthetic construction unit to an implant said apparatus comprising:

an implant control part;

at least one prosthetic construction unit control part cooperating with said at least one implant control part to impart to the prosthetic unit a distinct position on the implant;

at least one recess in each of said implant and construction unit control parts; and a securing element for installing in said recesses of said implant and construction unit control parts to extend in an essentially transverse direction to the implant;

wherein said securing element, when in the installed position, creates a pressing force against said construction unit control parts opposite a pressing force created by the securing element against said at least one implant control part in an axial direction of the unit and the implant, for pressing the construction unit against the implant; and wherein said securing element comprises a dual bearing in said at least one prosthetic construction unit control part and can cooperate, in its dual bearing suspension, with said implant control part via an eccentric part.

19. An apparatus for fixing a prosthetic construction unit to an implant comprising at least one implant control part;

at least one prosthetic construction unit control part cooperating with said at least one implant control part to impart to the prosthetic unit a distinct position on the implant;

at least one recess in each of said implant and construction unit control parts;

a securing element for installing in said recesses of said implant and construction unit control parts to extend in an essentially transverse direction to the implant;

wherein said securing element, when in the installed position, creates a pressing force against said construction unit control parts opposite a pressing force created by the securing element against said implant control parts in an axial direction of the unit and the implant, for pressing the construction unit against the implant; and wherein said implant control part has two portions arranged in parallel and which can be pushed over cooperating portions of a construction unit control part.

20. An apparatus for fixing a prosthetic construction unit to an implant said apparatus comprising:

at least one implant control part;

at least one prosthetic construction unit control part cooperating with said at least one implant control part to impart to the prosthetic unit a distinct position on the implant;

at least one recess in each of said implant and construction unit control parts;

a securing element for installing in said recesses of said implant and construction unit control parts to extend in an essentially transverse direction to the implant;

wherein said securing element, when in the installed position, creates a pressing force against said construction unit control parts opposite a pressing force created by the securing element against said implant control parts in an axial direction of the unit and the implant, for pressing the construction unit against the implant; and wherein either said implant control part or said construction unit control part includes two portions arranged in parallel, and wherein, when the unit is fixed to the implant, the two portions of said implant control part or said construction unit are displaced parallel to and over cooperating portions of said implant control unit or said construction unit control part.

21. An apparatus for fixing a prosthetic construction unit to an implant said apparatus comprising:

at least one implant control part;

at least one prosthetic construction unit control part cooperating with said at least one implant control part to impart to the prosthetic unit a distinct position on the implant;

at least one recess in each of said implant and construction unit control parts;

a securing element for installing in said recesses of said implant and construction unit control parts to extend in an essentially transverse direction to the implant;

wherein said securing element, when in the installed position, creates a pressing force against said construction unit control parts opposite a pressing force created by the securing element against said implant control parts in an axial direction of the unit and the implant, for pressing the construction unit against the implant; and wherein said implant control part comprises first and second locking portions, said locking portions being coupled to each other.

* * * * *